US008785715B2

(12) United States Patent
Wright et al.

(10) Patent No.: US 8,785,715 B2
(45) Date of Patent: Jul. 22, 2014

(54) ABSORBENT ARTICLE WITH A SLITTED ABSORBENT CORE

(75) Inventors: Andrew Wright, Chesterfield (GB); Patrick King Yu Tsang, Tuen Mun (HK)

(73) Assignee: DSG Technology Holdings, Ltd., Tortola (VG)

( * ) Notice: Subject to any disclaimer, the term of this patent is extended or adjusted under 35 U.S.C. 154(b) by 797 days.

(21) Appl. No.: 12/138,112

(22) Filed: Jun. 12, 2008

(65) Prior Publication Data

US 2009/0062760 A1    Mar. 5, 2009

Related U.S. Application Data

(60) Provisional application No. 60/943,321, filed on Jun. 12, 2007.

(51) Int. Cl.
*A61F 13/15*  (2006.01)

(52) U.S. Cl.
USPC ............ 604/378; 604/379; 604/380; 604/383

(58) Field of Classification Search
USPC .................................. 604/378, 379, 380, 383
See application file for complete search history.

(56) References Cited

U.S. PATENT DOCUMENTS

| | | | |
|---|---|---|---|
| 2002/0169428 A1* | 11/2002 | Fell et al. ...................... 604/367 |
| 2006/0047257 A1 | 3/2006 | Raidel et al. | |
| 2007/0135785 A1* | 6/2007 | Qin et al. ...................... 604/368 |
| 2007/0135787 A1 | 6/2007 | Raidel et al. | |

FOREIGN PATENT DOCUMENTS

| | | |
|---|---|---|
| EP | 1634556 A | 3/2006 |
| WO | WO-2005/110319 A | 11/2005 |
| WO | PCT/IB2008/001517 | 6/2008 |

OTHER PUBLICATIONS

International Search Report issued during the prosecution of International Application No. PCT/IB2008/001517.
Written Opinion issued during the prosecution of International Application No. PCT/IB2008/001517.
Examination Communication from European Patent Office, Application 08762850.9, issued Dec. 8, 2011, 4 pages.
Office Communication issued in Mexican Application No. MX/a/2009/013415, dated Sep. 12, 2012.
Office Communication in Malaysian Patent Application No. PI 20095209 filed Jun. 12, 2008, mailed Dec. 31, 2012.
First Office Action from foreign proceedings of CN200880102735.8, issued May 30, 2012, 58 pages. (Translation provided).

* cited by examiner

*Primary Examiner* — Jacqueline F. Stephens
(74) *Attorney, Agent, or Firm* — Fulbright & Jaworski LLP

(57) ABSTRACT

The invention relates to slit absorbent articles and the use of slits in absorbent materials to provide improved liquid intake rate, flexibility and softness compared to the unmodified material. The absorbent material, including superabsorbent materials, are particularly useful as absorbent cores in disposable absorbent articles such as diapers, incontinent products, sanitary napkins and the like.

16 Claims, 7 Drawing Sheets

ABSORBENT ARTICLE WITH A SLITTED ABSORBENT CORE

CROSS-REFERENCE TO RELATED APPLICATIONS

This application claims priority under 35 U.S.C. 119(e) from provisional U.S. Patent Application No. 60/094,321 filed Jun. 12, 2007 the contents of which are incorporated herein by reference.

TECHNICAL FIELD

The present invention relates to liquid absorbing articles incorporating superabsorbents and, more particularly, to the use of slits in the absorbent core to provide the requisite properties of fast fluid intake, thinness, flexibility and softness.

BACKGROUND OF THE INVENTION

Absorbent articles such as disposable diapers, adult incontinent pads, sanitary napkins and the like are generally provided with an absorbent core material to receive and retain body liquids. Typical compositions of absorbent core materials are particulate, absorbent, polymeric compositions, often referred to as "hydrogels" or "superabsorbents", which are capable of absorbing large quantities of liquids such as water and body exudates. Fibrous components such as pulp or other synthetic fibers are incorporated into the composite together with the superabsorbent to provide acceptable fluid handling characteristics of fast liquid intake, liquid capture and reduced "gel blocking". Gel blocking is a phenomenon that occurs when the swelling of the absorbent particles as a result of liquid absorption increases the resistance to liquid flow within the material. It is generally believed that the fibrous component provides stable interparticle liquid channels that minimize the gel blocking effect.

For fit, comfort and aesthetic reasons, it is highly desired to make disposable absorbent articles as thin as possible. Disposable absorbent articles can be reduced in thickness by reducing the absorbent core thickness. Thinner diapers are less bulky to wear, fit better and provide more comfort to the wearer. To achieve the lowest absorbent core thickness for a given level of absorbent capacity, the superabsorbent content is preferably increased toward 100%, that is, the fiber component of the absorbent core is reduced to near zero percent. The composite of superabsorbent content and fiber component oftentimes is also subjected to densification to achieve and maintain reduced thickness. However, such absorbent composites generally display much slower liquid intake characteristics due to their high composite density, high gel blocking characteristics, low permeability to liquid passage that that cause liquid leakage. In addition, higher stiffness and rigidity of such structures lead to absorbent products with poor fit and comfort.

As disclosed in prior art, the slower liquid intake of superabsorbent-containing absorbent cores can be compensated for by adding liquid-holding layers of materials on top of the absorbent core. These are usually fibrous or film structures capable of accepting the liquid insult at its rate of delivery and temporarily holding the liquid until the absorbent core can fully absorb and retain the insult. These elements are termed surge or acquisition layers, as shown in U.S. Pat. No. 5,364,382. However, increasing the number of surge layers to compensate for a much slower absorbing core adds to the thickness and cost of the absorbent article.

Other approaches such as discontinuous and patterned placement of the superabsorbent material or composite have been disclosed in the art, such as U.S. Pat. Nos. 4,560,372 and 5,868,724. Voids are created in the absorbent composite, hence the surface coverage of the absorbent composite is less than 100%. Implementation of approaches is relatively complex. Furthermore the full area available for absorbency is not utilized, and consequently the article is thicker than one with a relatively uniform distribution of superabsorbent material.

Hence, there remains a need for an absorbent core that is thin, having high absorbent capacity with good fluid intake rate characteristics, soft, and flexible that can be used in absorbent articles such as disposable diapers, adult incontinent pads or briefs, sanitary napkins and the like.

BRIEF SUMMARY OF THE INVENTION

The present invention is directed to the use of one or more slits within an absorbent composite of a disposable absorbent article. The one or more slits provide for high performance disposable absorbent articles which are thin, soft and flexible. Such an absorbent composite may be employed as the primary component of the absorbent core, together with a topsheet, a backsheet, containment walls or cuffs, and other elements (e.g., an acquisition layer) of the disposable absorbent article. Among the characteristics which may be exhibited by embodiments of the inventive absorbent article are improved fit and appearance, improved absorption and liquid containment properties, simpler, more efficient manufacturing process, and a thinner, more compact construction.

It is therefore an object of the invention to provide a disposable absorbent article having improved overall thinness, improved rate of liquid acquisition, and with an absorbent core which is soft and flexible.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

It has been discovered that the addition of an adequate level of slitting to a absorbent composite causes a significant improvement in its liquid intake and a corresponding increase in softness and flexibility without an increase in composite thickness and without a reduction of machine direction (MD) strength. Machine direction strength is particularly advantageous to the manufacturing and processing of the absorbent articles.

For purposes of increasing liquid intake, the appropriate level of slitting should be greater than 0.1. By definition, a material that does not contain any slits has a "slit level" of zero. The level of slitting can be determined by summing the total slit perimeter formed from the multiplicity of slits used and normalizing the total slit perimeter to the planar area of the composite encompassing the slit region. For example, 5 slits that are 1 cm in length distributed in a 5 cm×10 cm area of the absorbent would yield a slit level of 0.2 cm$^{-1}$. In this example, the total slit perimeter is 1 cm×2×5=10 cm; planar area is 5 cm×10 cm=50 cm$^2$; and slit level is 10 cm/50 cm$^2$=0.2 cm$^{-1}$. For purposes of increasing softness and flexibility, the slit size and placement can be distributed according to a pattern that yields the appropriate improvement. In general, a higher slit level leads to both faster intake and higher softness and flexibility.

Figure 2A:
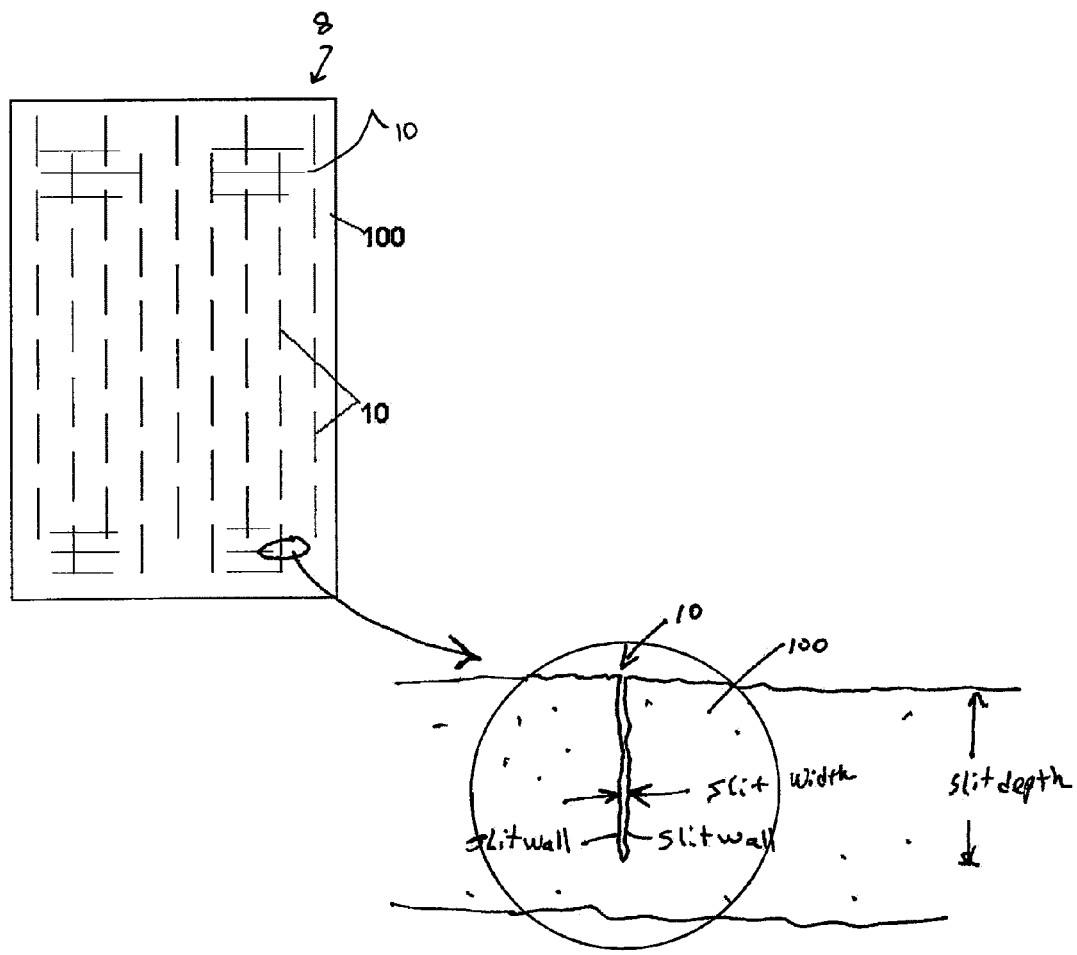
FIG. 2A is a top plan view of an absorbent core with a multiplicity of slits arranged in various patterns along the machine direction (MD) and cross direction (CD) wherein the slit is a partial slit traversing a portion of the full absorbent core thickness.
Figure 2B:
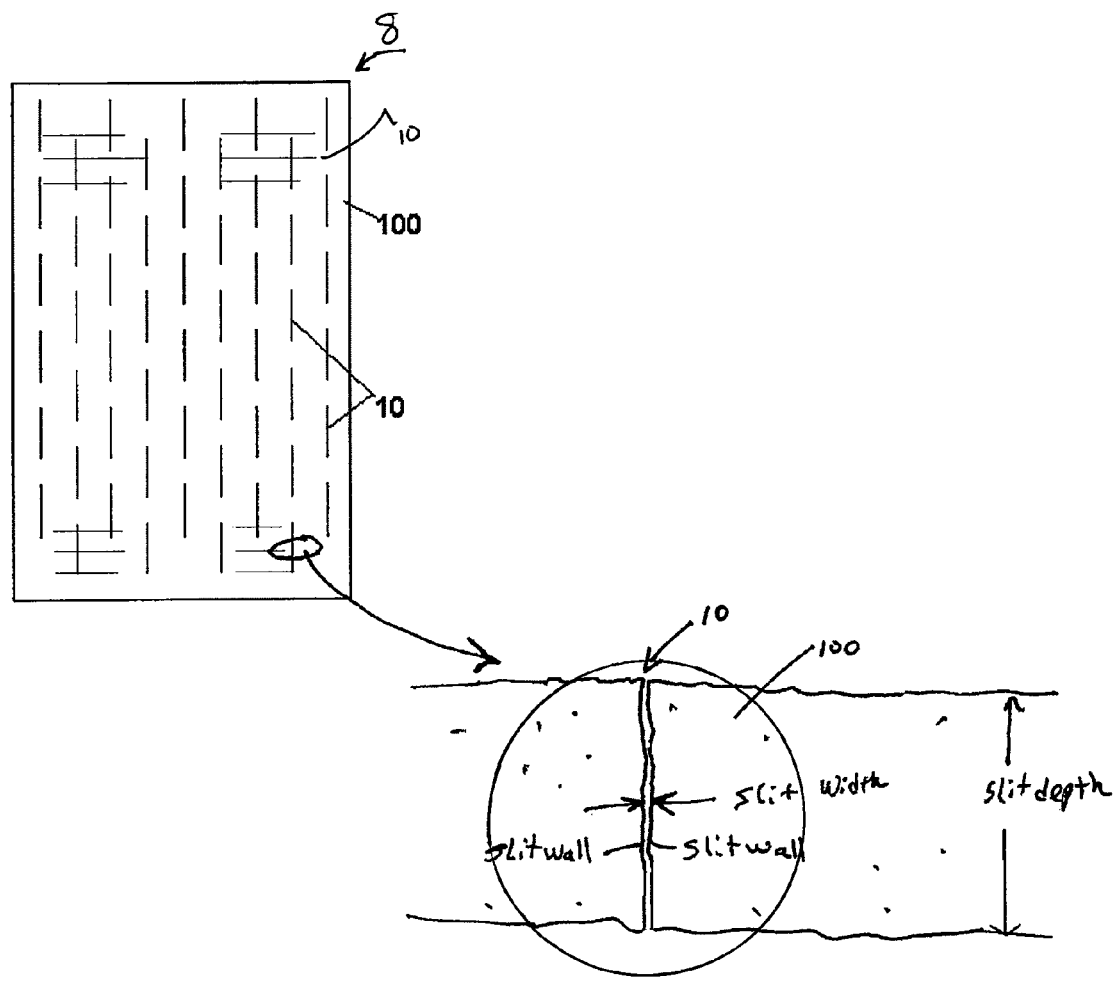
FIG. 2B is a top plan view of an absorbent core with a multiplicity of slits arranged in various patterns along the machine direction (MD) and cross direction (CD) wherein the slit is a through slit traversing the full absorbent core thickness.

As used herein, the term "slit" is defined as a narrow cut, opening or aperture. The slit may be straight or curved and may be disposed in any planar orientation within the absorbent composite, including vertical or angled relative to the top surface. The slit depth may vary between slits and may also vary along a slit length. The slit depth can be equal to the thickness of the absorbent core. Such slits can be referred to as "partial slits", such as shown in FIG. 2A or as "through slits", such as shown in FIG. 2B. During manufacturing of the absorbent article, the slitting of the absorbent core may take place before or after the absorbent core is connected to a back sheet.

Without being bound by theory, it is believed that the slit regions have higher liquid intake rate compared to the non-slit areas due to an increase in liquid permeability and an increase in surface area around the slit. Similarly, slits provide a material discontinuity and a region of zero or very low modulus that facilitates the bending or folding of the absorbent core along the slit region also resulting in a macroscopically flexible material. It is also possible that the slits facilitate capillary flow of liquid toward an interior of the absorbent core. Slit widths, defined as the distance between walls of a slit, may range from about 1 micron to about 1000 microns.

Appropriately placed slits in the absorbent core provide bend and fold lines that can be utilized in creating shaped absorbent cores from rectangular absorbent composites resulting in simpler and more efficient manufacturing processes. For example, in a diaper, long slits placed along the crotch area and towards the side edges of the absorbent core enables the folding inward of these outboard edges creating an "hourglass" shaped absorbent core that can provide enhanced fit. Moreover, because of such folding, more absorbent composite is added to the target area, and a bumper-like absorbent structure is created that can reduce leakage in the crotch area.

Other areas in the absorbent core can be selectively slit to provide the desired bending characteristics that enable the absorbent article to follow the body curvature for improved fit and appearance.

Slitting may be accomplished through shear, score or burst slitting such as provided by rotating or stationary knives, cutting dies, laser or water jet cutting. The absorbent material may also be subjected to mechanical softening prior to the addition of slits. Examples of such softening processes are creping, groove or ring-rolling, and embossing.

Figure 1:
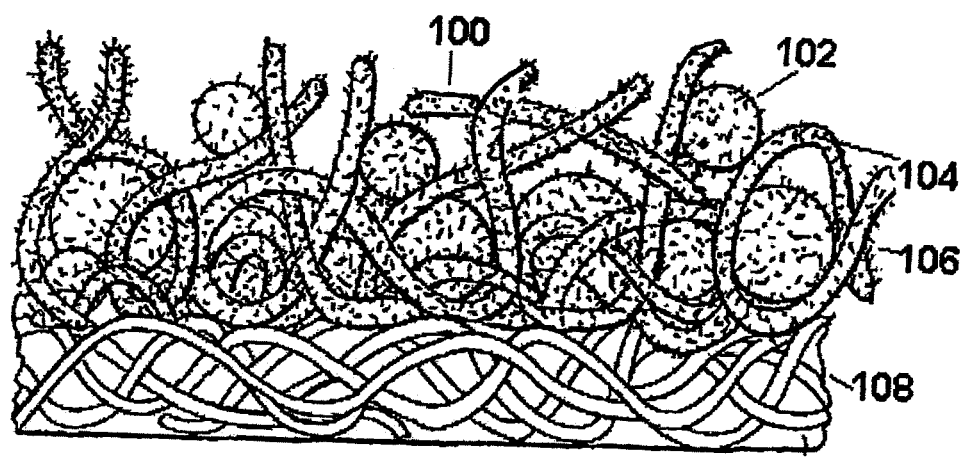
FIG. 1 is a vertical cross-section illustration of the absorbent composite used as absorbent core.

FIG. 1 depicts a magnified illustration of an absorbent composite or core 100 used in an embodiment of the present invention. Core 100 may define one or more layers within an absorbent core of a disposable absorbent article 8, as shown in FIG. 2A. Core 100 includes superabsorbent particles 102 which are covered or intermixed with extremely fine microfibrillated cellulose (MFC) 104, embedded into the pores of a low-density nonwoven substrate 106 and a high density layer 108 of the nonwoven substrate 106. The superabsorbent content is preferably from 70-95%. A process of manufacturing the absorbent core 100 has been developed by the Japan Absorbent Technology Institute (JATI) and available under the trade name MEGATHIN. The details of the manufacturing process and other characteristics of the MEGATHIN sheet are described in U.S. Pat. No. 6,790,798, hereby incorporated by reference. In particular, in one embodiment, the absorbent composite or core 100 comprises: a non-woven fabric substrate having a bulky structure; solid SAP partly contained inside said bulky structure and partly disposed on a surface of said non-woven substrate; and a fibrous network in a form of a mesh formed of a hot-melt adhesive as a thermally fusible component, said fibrous network contacting and covering said solid SAP to trap and hold the solid SAP so that said solid SAP is held in position. In another embodiment, the absorbent composite or core 100 comprises a non-woven substrate, a SAP layer, and a fibrous network in a form of a mesh formed of a hot-melt adhesive layer as a thermally fusible component, said fibrous network contacting and substantially entirely covering said SAP layer to trap and hold the SAP layer, and a sheet material disposed on said adhesive layer and bonded with said composite absorbent by said hot-melt adhesive layer by an adhesive property thereof to form a composite structure. In another embodiment, absorbent composite or core 100 comprises first and second composite absorbents, each comprising a non-woven substrate, an SAP layer, and a fibrous network in a form of a mesh formed of a hot-melt adhesive layer as a thermally fusible component, said fibrous network contacting and covering said SAP layer to trap and hold the SAP layer, said first composite absorbent being laid on the second composite absorbent such that said hot-melt adhesive layers contact with each other and are bonded together by an adhesive property thereof to form a two material composite structure. In yet another embodiment, absorbent composite or core 100 comprises a non-woven substrate including a non-woven fabric with voids therein, solid SAP partly disposed in the voids and distributed almost all over in a layer on a surface of the non-woven fabric, and a dual fibrous network contacting and covering a surface of the solid SAP to trap and hold the solid SAP, said dual fibrous network having a first fibrous network in a form of dense mesh comprising a hot-melt adhesive as a thermally fusible component and a second fibrous network in a form of loose mesh coarser than the dense mesh and positioned over said first fibrous network.

The absorbent core 100 may include one or more layers or strata of natural or synthetic fibers. Superabsorbent polymers (SAP) may be incorporated into the absorbent layer as particles, granules, flakes, etc., and may be included as a discrete stratum or mixed with the aforementioned fibers. SAP particles of various type, size or shape suitable for use in an absorbent core may be employed in embodiments of the invention. Materials such as fillers, perfumes, surfactants, and additives may be included in the absorbent composite. In a preferred embodiment, the absorbent composite contains 50-97% by weight of SAP and 3-50% by weight of fibers. More preferred embodiments of the present invention include polyacrylate-based SAPs and resilient fibers such as polyester (PET), polyolefin (PP or PE), or nylon fibers (Hydrofil™).

Basis weights of the absorbent composite can be adjusted and optimized for particular purposes over a wide range. Furthermore, multiple layers of the absorbent composite can be assembled to achieve the desired total basis weight. Generally, the basis weight of a single absorbent composite layer can range, for example, from about 50 grams per square meter (gsm) to about 1000 gsm, and more specifically from about 100 to 500 gsm.

In preferred embodiments of the present invention, the absorbent core 100 (or layer portions thereof) is slit according to a predetermined pattern to increase fluid intake rate and flexibility. The absorbent core 100 may include multiple layers, with slit patterns being different between layers. In one embodiment, core 100 includes two or more layers, with at least one layer having a slit pattern and another layer having substantially no slits.

FIG. 2A and FIG. 2B are top plan views of an absorbent core 100 with a multiplicity of short slits 10 arranged in various patterns along the machine direction (MD) and cross direction (CD). As noted previously, the number and length of the slits can be varied to deliver the intake performance and flexibility required. In this embodiment, a slit level of at least 0.1 cm$^{-1}$ and a slit length of at least 0.2 cm is required.

Figure 3:
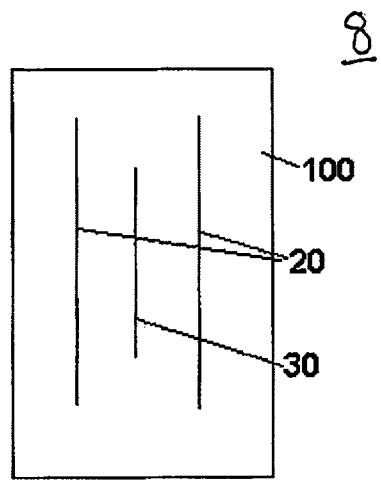
FIG. 3 is a top plan view of an arrangement of an embodiment of the present invention having an absorbent core with long side slits to achieve side bending.

Another exemplary embodiment is shown in FIG. 3. The particular arrangement of the three slits, two long side slits 20 and center slit 30 encourages the folding of the absorbent core to form of an absorbent bucket that effectively reduces early leakage.

Figure 4:
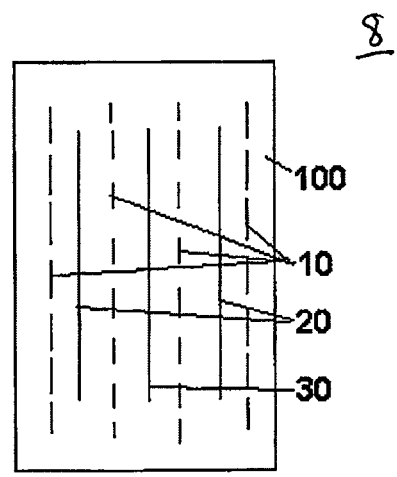
FIG. 4 is a top plan view of an absorbent core with center and side slits and a multiplicity of smaller slits placed between the long slits.

FIG. 4 is another embodiment of the present invention with long center slit 30 and side slits 20, together with a multiplicity of smaller slits 10 placed between the long slits 20 and 30, to achieve higher liquid intake rates in addition to preferentially bucket formation.

Figure 5:
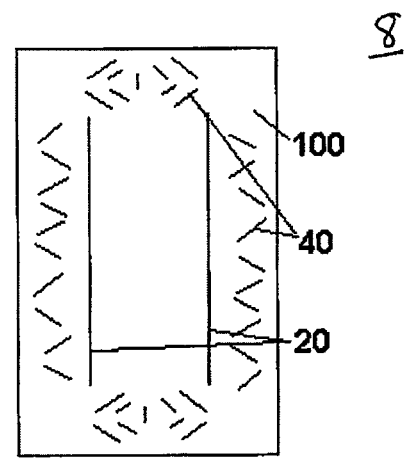
FIG. 5 is a top plan view of an absorbent core with patterned slits at ends and sides in addition to long side slits.
Figure 6:
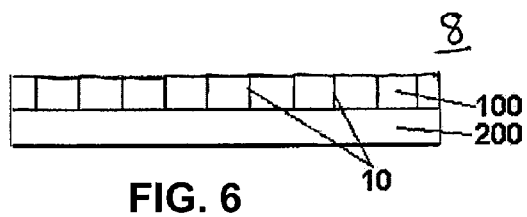
FIG. 6 is a cross sectional view along the transverse direction of a layered absorbent composite showing a slit absorbent core as a top layer over an unslit absorbent core as a lower layer.

FIG. 5 is a top plan view of absorbent core 100 with patterned slits 40 at ends and sides in addition to long side slits 20. Slits patterned towards the ends of the product provide faster intake rates in those regions and hence reduce waist leakage. Absorbent core 100 construction may also include more than one absorbent composite layer. For example, a two-layer absorbent core structure can be assembled wherein the top layer 100 is slit 20 for enhanced intake and the bottom absorbent 200 remains unslit. FIG. 6 is a cross sectional view taken along the transverse direction view of such a layered absorbent core structure. An example of the present invention may include a liquid pervious top sheet or an acquisition layer or both.

Figure 7:
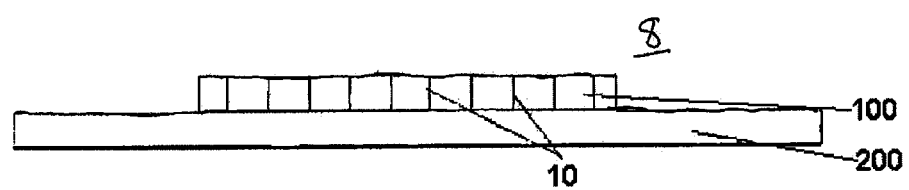
FIG. 7 is a cross sectional view along the longitudinal direction of a layered absorbent composite showing a slit absorbent core as an upper layer positioned around the liquid target region and an unslit absorbent core as lower layer absorbent composite.

FIG. 7 is a cross sectional view taken along the longitudinal direction of an absorbent article such as a diaper of a two-layer absorbent core structure described by FIG. 6 and depicting the placement of the inventive slit structure centrally around the crotch area only.

Figure 8:
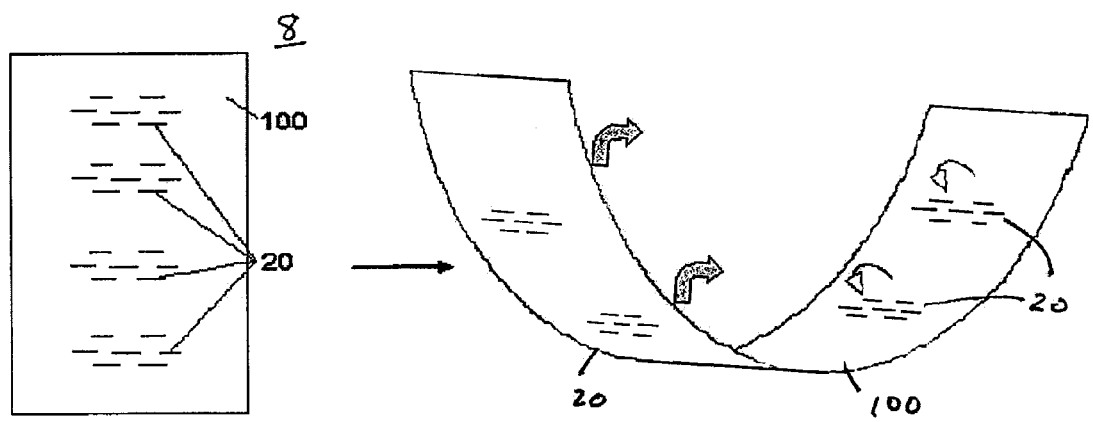
FIG. 8 depicts a top plan view and a perspective view of appropriately placed slits in the absorbent composite that provide bend areas and enable the absorbent article to follow the body curvature.

FIG. 8 illustrates the use of appropriately disposed slits 20 to provide bend areas that enable the absorbent article to follow the body curvature for improved fit and appearance.

Figure 9:
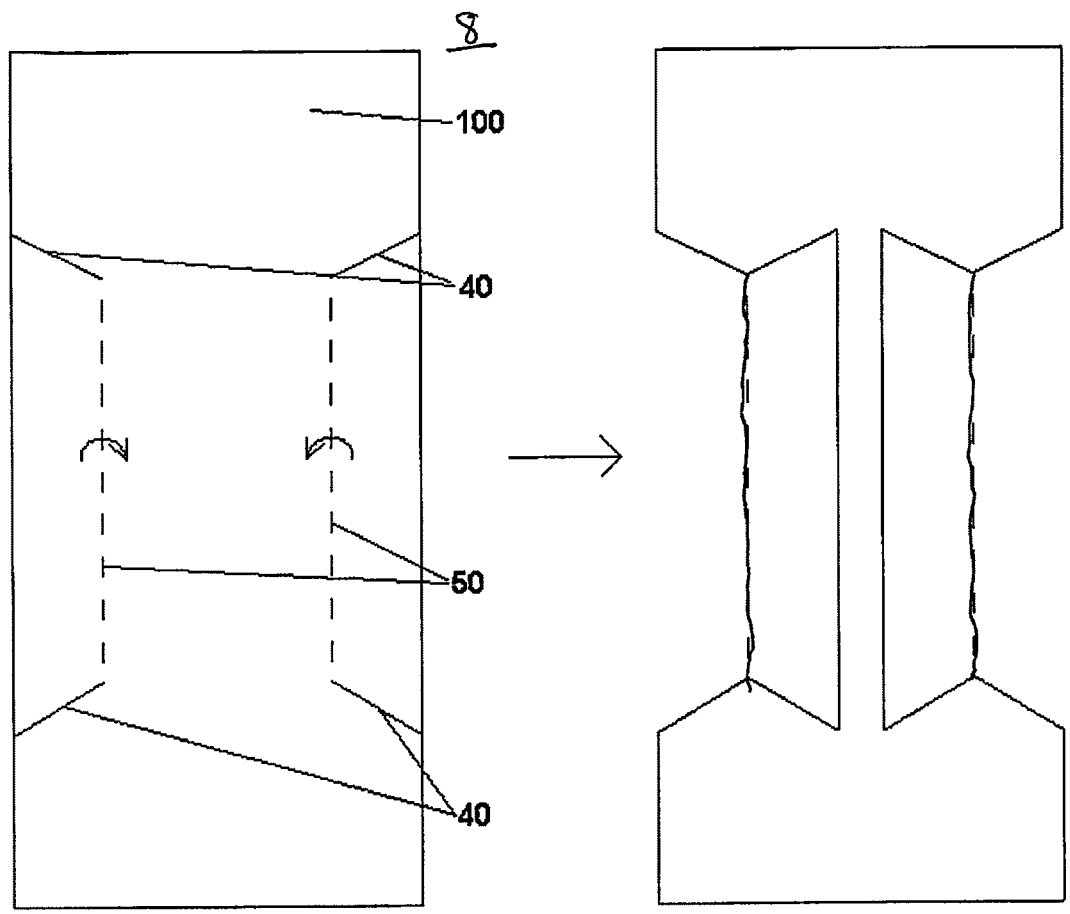
FIGS. 9 and 10 are top plan views of shaped absorbents derived from a rectangular absorbent core through slitting and folding.
Figure 10:
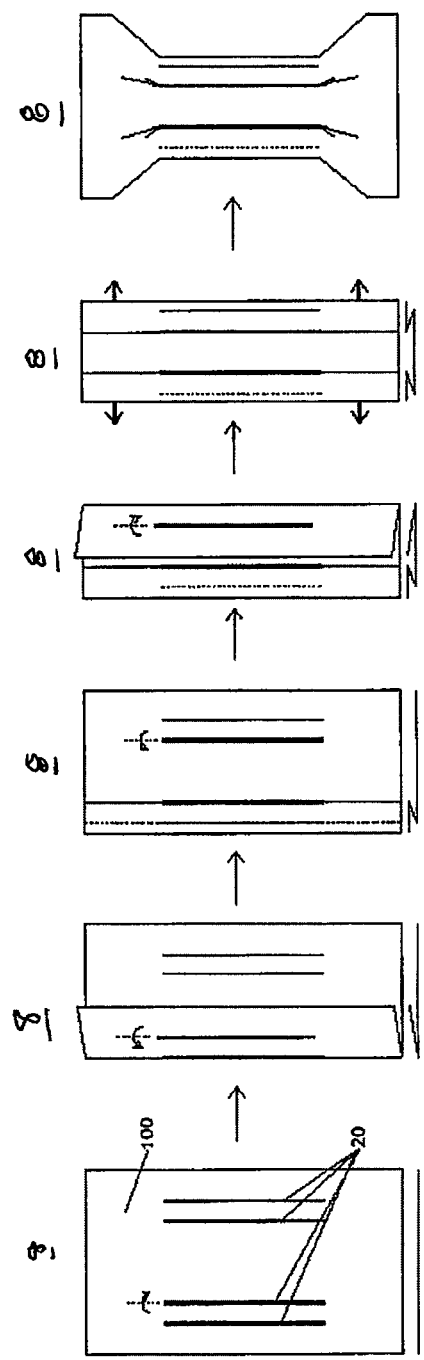

In another embodiment illustrated by FIG. 9, appropriately placed slits in the absorbent core 100 provide cut 40 and bend/fold lines 50 and yield a hourglass shaped absorbent composite from a rectangular absorbent composite. Similarly FIG. 10 depicts an hourglass shaped absorbent composite created by slitting and folding along slit lines 20.

Exemplary embodiments of the present invention were subjected to experimentation. Descriptions of the test procedures follows.

Intake Rate

Intake rate is determined using the liquid strikethrough test. The test determines the time required for an absorbent composite to intake a preset amount of liquid. A reduction in liquid strikethrough time indicates an improvement in intake rate. The liquid strike through time is measured using the known Fluid Intake Flowback Evaluation (FIFE)-type test apparatus. In a typical experiment, three consecutive 40 ml quantities of test liquid (e.g., 0.9% saline solution) are applied to the absorbent core sample at 15 minute intervals and the respective strikethrough times are recorded.

Flexibility

Flexibility is determined using the drape stiffness test. This test determines the bending length of a material subject to cantilever bending without application of external forces. What is measured is the drape stiffness or resistance to bending of the material. Bending length is a measure of the interaction between material weight and material stiffness as shown by the way in which a fabric or a sheet bends under its own weight. This is a reflection of the stiffness of a planar material when bent in one plane under the force of gravity.

For example, a 10 cm×5 cm specimen was slid, in a direction parallel to its long dimension, so that its leading edge projected from the edge of a horizontal surface. At predetermined lengths of specimen pushed past the leading edge of the horizontal surface, the vertical distance between the horizontal surface and the tip of the bent specimen was measured. This vertical distance is commonly referred to as the material's bending length or flexibility. The greater the bending length, the easier the material is to bend. Thus higher bending lengths indicate a more flexible material. Materials can be tested for flexibility along the MD or cross direction (CD).

EXAMPLES

Column 1 of Table 1 provides the absorbent composites used in the accompanying examples in accordance with the present invention. These composites had a very high superabsorbent content, are thin and have a high composite density. The corresponding bulk density, calculated as the reciprocal of composite density is low, indicative of the thinness of the composite. The superabsorbent used was a polyacrylate-based SAP with a centrifuge retention capacity (CRC) of about 36 g/g, a free swell capacity of about 53 g/g, and an average particle diameter of 200-300 microns.

TABLE 1

| | Superabsorbent (SAP) | SAP basis wt, gsm | Fiber components | Fiber components basis wt, gsm | % SAP in composite | Total absorbent basis wt, gsm | Thickness, cm | Density g/cc | Bulk Density, cc/g |
|---|---|---|---|---|---|---|---|---|---|
| 1 | Nippon Shokubai | 125 | 92% PET, 8% MFC | 30 | 80.65% | 155 | 0.03 | 0.52 | 1.94 |
| 2 | Nippon Shokubai | 250 | 92% PET, 8% MFC | 95 | 72.46% | 345 | 0.075 | 0.46 | 2.17 |

TABLE 2

| Absorbent | Top Layer | Slit Level $cm^{-1}$ | CD Flexibility, cm | Bottom Layer | Strikethrough time (s) 1 | 2 | 3 |
|---|---|---|---|---|---|---|---|
| Top and bottom layers: 125 gsm MEGATHIN ™, 80% SAP, 20% fiber, mechanically softened | slit | 1.66 | 2.32 | not slit | 18.1 | 34.45 | 39.8 |
| Top and bottom layers: 125 gsm MEGATHIN ™, 80% SAP, 20% fiber, mechanically softened | not slit | 0 | 1.66 | not slit | 33.55 | 38.75 | 40.25 |
| | | Effect of slitting top layer: % improvement in strikethrough time | | | 46.05% | 11.10% | 1.12% |

The effect of slitting the absorbent core on intake rate and flexibility is shown in Table 2. Two layers of the absorbent composite were used. In this dual layer absorbent core construction, only the top absorbent layer was slit. A slit length of 1.2 cm and a slit pattern similar to the pattern in FIG. 2 was used. The slits were oriented in the machine direction (MD), staggered, spaced 0.6 cm apart in the MD and spaced 0.8 cm in the cross direction (CD). The slit level for this slit pattern was 1.66 cm$^{-1}$. The absorbent composites were also mechanically pre-softened by passing the composites through an embossing unit with intermeshed gears. The CD bending length at a 4 cm overhang (i.e., 4 cm of the inventive absorbent composite along its CD direction was projected past the edge of the horizontal surface) was measured and reported as the composite flexibility.

It is readily seen that the absorbent composite subjected to slitting according to the present invention had a significantly improved intake rate and flexibility.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An absorbent article having a front waist region, a back waist region, and a crotch region extending longitudinally between said front and back waist regions, said article comprising:
    a liquid impervious back sheet; and
    an absorbent core comprising:
        at least one absorbent layer of comprising superabsorbent material and a plurality of slits disposed in the at least one absorbent layer, said plurality of slits extending through at least a portion of the at least one absorbent layer, said plurality of slits facilitating greater liquid intake of said at least one absorbent layer as compared to an identical, but non-slitted, layer, and further facilitating improved flexibility of the at least one absorbent layer in a predetermined direction;
        wherein the absorbent core comprises from about 61% to about 97% by weight of a superabsorbent material, from about 3% to about 39% by weight of non-absorbent nonwoven resilient fibers, and 0% by weight of absorbent hydrophilic fibers, wherein the superabsorbent material comprises particles and the non-absorbent nonwoven resilient fibers form a low-density layer and a high-density layer.

2. The absorbent article of claim 1 wherein at least some of the plurality of slits extend from a top surface of the at least one absorbent layer towards the back sheet.

3. The absorbent article of claim 2 further comprising at least one of a top sheet and an acquisition layer.

4. The absorbent article in claim 1 wherein said plurality of slits comprise a slit level greater than 0.1 cm$^{-1}$ wherein said slit level is determined at least by a total perimeter of said plurality of slits normalized to a planar area of said absorbent core.

5. The absorbent article of claim 1 wherein said absorbent layer has a basis weight from about 50 grams per square meter (gsm) to about 1000 gsm.

6. The absorbent article of claim 5 wherein said absorbent material layer has a basis weight from about 100 gsm to about 500 gsm.

7. The absorbent article of claim 1 wherein the at least one absorbent layer is folded along at least one region of material discontinuity.

8. The absorbent article in claim 1 wherein said at least one absorbent layer is subjected to a mechanical softening process.

9. The absorbent article of claim 1 wherein the at least one absorbent layer is folded along two or more lines of material discontinuity, wherein said two or more lines are oriented in a product longitudinal direction and located about a central region of the absorbent article, thereby defining an hourglass shape.

10. The absorbent article in claim 1 with the absorbent core further comprising: another absorbent layer comprising superabsorbent material, said another absorbent layer having substantially fewer slits as compared to the at least one absorbent layer.

11. The absorbent article of claim 1 wherein said plurality of slits comprise a slit width of between 1 micron and 1000 microns to support a capillary flow of liquid into an interior of the at least one absorbent layer.

12. The absorbent article of claim 11 wherein more than one of said plurality of slits extend along a substantial portion of a side of the absorbent core.

13. The absorbent article of claim 12 wherein said more than one of said plurality of slits extend longitudinally between said front waist region and said back waist region.

14. The absorbent article of claim 11, wherein the plurality of slits comprises a slit width between about 1 micron and about 500 microns.

15. The absorbent article of claim 1, wherein the plurality of slits comprises a first group of slits in a first bend area and a second group of intersecting slits in a second bend area, wherein the first group is spaced apart from the second group.

16. A disposable absorbent article having a front waist region, a back waist region, and a crotch region extending longitudinally between said front and back waist regions, said article comprising:
an absorbent core comprising:
from about 61% to about 97% by weight of a superabsorbent material, from about 3% to about 39% by weight of non-absorbent nonwoven resilient fibers, and 0% by weight of absorbent hydrophilic fibers;
and a first absorbent layer comprising a modified region, said modified region having a higher fluid intake rate as compared to an unmodified region;
wherein said modified region comprises a plurality of slits disposed in said first absorbent layer, said plurality of slits extending through at least a portion of said first absorbent layer, said slits promoting the higher fluid intake rate in at least the modified region;
wherein the superabsorbent material comprises particles and the non-absorbent nonwoven resilient fibers form a low-density layer and a high-density layer.

* * * * *